US006721583B1

(12) United States Patent
Durkin et al.

(10) Patent No.: US 6,721,583 B1
(45) Date of Patent: Apr. 13, 2004

(54) METHOD FOR NON-INVASIVE IDENTIFICATION OF INDIVIDUALS AT RISK FOR DIABETES

(75) Inventors: Anthony J. Durkin, Irvine, CA (US); Marwood N. Ediger, Vienna, VA (US); Vivian M. Chenault, Gaithersburg, MD (US)

(73) Assignee: The United States of America, Washington, DC (US)

( * ) Notice: Subject to any disclaimer, the term of this patent is extended or adjusted under 35 U.S.C. 154(b) by 0 days.

(21) Appl. No.: 09/856,186

(22) PCT Filed: Nov. 18, 1999

(86) PCT No.: PCT/US99/27360
§ 371 (c)(1),
(2), (4) Date: Mar. 20, 2002

Related U.S. Application Data
(60) Provisional application No. 60/109,257, filed on Nov. 19, 1998.

(51) Int. Cl.[7] ................................................. A61B 5/00
(52) U.S. Cl. ........................ 600/318; 600/476; 600/473; 600/310
(58) Field of Search ................................. 600/309–310, 600/322–326, 316, 317, 318–320, 407, 476, 473, 321

(56) References Cited

U.S. PATENT DOCUMENTS

| | | | | |
|---|---|---|---|---|
| 5,243,983 A | * | 9/1993 | Tarr et al. | 600/318 |
| 5,553,617 A | * | 9/1996 | Barkenhagen | 600/318 |
| 5,582,168 A | * | 12/1996 | Samuels et al. | 600/407 |
| 5,873,831 A | * | 2/1999 | Bernstein et al. | 600/473 |
| 5,885,224 A | * | 3/1999 | Yoshida | 600/558 |
| 5,973,779 A | * | 10/1999 | Ansari et al. | 356/301 |
| 6,044,285 A | * | 3/2000 | Chaiken et al. | 600/316 |
| 6,181,957 B1 | * | 1/2001 | Lambert et al. | 600/319 |
| 6,505,059 B1 | * | 1/2003 | Kollias et al. | 600/316 |

* cited by examiner

*Primary Examiner*—Max F. Hindenburg
*Assistant Examiner*—Matthew Kremer
(74) *Attorney, Agent, or Firm*—Merchant & Gould P.C.

(57) ABSTRACT

The invention provides methods for the use of Raman spectroscopy to non-invasively detect molecular characteristics of the constituents of the aqueous humor, vitreous humor, lens or retina. The method can be employed for the detection of molecular changes underlying ocular pathologies. In one embodiment of the invention, the method involves the steps of introducing light into the eye of the subject using a laser; collecting Raman spectra emitted from the eye; dispersing the collected Raman spectra onto a detector; and analyzing detected Raman spectral data to identify a molecular change related to an ocular pathology. The non-invasive method provided by the invention makes use of techniques and equipment that enable detection of Raman spectra with light intensities that fall within acceptable safety standards.

53 Claims, 2 Drawing Sheets

METHOD FOR NON-INVASIVE IDENTIFICATION OF INDIVIDUALS AT RISK FOR DIABETES

This application 15 a 371 of application Ser. No. PCT/US599/27360 filed Nov. 18, 1999.

TECHNICAL FIELD OF INVENTION

The invention relates to methods for non-invasive detection of ocular pathologies. More particularly, the invention provides a non-invasive method for detecting molecular changes in the eye of a subject that are associated with an ocular pathology. The method can be used for the identification of diabetes-associated molecular changes and the identification of individuals at risk for developing diabetes.

BACKGROUND OF THE INVENTION

Diabetes mellitus is a complex group of syndromes that have in common a disturbance in the oxidation and utilization of glucose, which is secondary to a malfunction of pancreatic beta cells. One of the most threatening aspects of diabetes mellitus is the development of visual impairment or blindness consequent to cataract formation, retinopathy or glaucoma. Diabetes-related ocular pathologies often go undiagnosed until visual function is compromised.

There is a need for non-invasive methods for prospective identification of individuals at risk for developing diabetes and for identifying ocular pathology in its earliest stages. Non-invasive methods will require techniques which avoid exposing the eye to unsafe light intensities while still producing data capable of detection and analysis. References describing techniques relevant to non-invasive ocular measurements, including Raman spectroscopy, include J. Sebag et al., 1994, Invest. Ophthamol. Vis. Sci., 35(7):2976–2980; Y. Ozaki et al. 1987, Applied Spectroscopy 41(4):597–605; A. Mizuno and Y. Ozaki, 1991, Lens and Eye Toxicity Research, 8:177–187; N. T. Yu and E. J. East, 1975, J. Biol. Chem. 250:2196–2202; N. T. Yu and E. J. East, Current Eye Research, 1(10):615–618; Y. Ozaki et al., 1987, Applied Spectroscopy, 47(7):1245–1247; S. Toshima et al., 1990, Ophthalmol., 344:436–441; A. Mizuno et al., 1990, Exp. Eye. Res., 50:647–49; I. Seibinga et al., 1992, Exp. Eye. Res. 54:759–767; J. P. Wicksted et al., 1995, Appl. Spec., 49:987–993; R. R. Ansari et al., 1996, Ophthalmic Technologies VI, pp. 12–20; R. R. Ansari et al., 1996, Lasers in Ophthalmology III, pp. 62–72; R. R. Ansari; N.J. Bauer et al., 1998, IVOS, 39(5), pp 831–835, and K. I. Suh, 1996, Optical Diagnostics of Living Cells and Biofluids, Vol. 2678.

SUMMARY

The invention provides methods for the use of Raman spectroscopy to non-invasively detect molecular characteristics of the constituents of the aqueous humor, vitreous humor, lens or retina. The method can be employed for the detection of molecular changes underlying ocular pathologies. The non-invasive method provided by the invention makes use of techniques and equipment that enable detection of Raman spectra with light intensities that fall within acceptable safety standards.

The methods disclosed herein encompass a variety of embodiments. In one embodiment of the invention, the method involves the steps of introducing light into the eye of the subject using a laser; collecting Raman spectra emitted from the eye; dispersing the collected Raman spectra onto a detector; and analyzing detected Raman spectra to quantify a molecular change related to an ocular pathology. In a preferred embodiment, the method is employed to detect early markers of diabetes or diabetes-induced ocular pathologies. In highly preferred embodiments of the invention, the ocular pathology is a pre-cataract marker or a pre-retinopathy marker. In a variation of this embodiment, the method further involves correlating the Raman spectra with traditional markers associated with known ocular pathologies. In an illustrative embodiment, the markers associated with diabetes induced ocular pathologies include blood glucose and insulin levels.

In other embodiments of the invention, detected Raman spectra obtained from a subject suffering from an ocular pathology is analyzed and compared to a normal spectral pattern in order to identify a molecular change that is associated an ocular pathology. In a specific embodiment of this method, the subject is a sand rat and the ocular pathology is diabetes induced ocular damage. In a related embodiment, Raman spectroscopic measures obtained from a patient can be compared to a data set range of measures established from subjects with normal to severely pathological ocular measures to determine the current status of the subject's condition.

DETAILED DESCRIPTION

Figure 1:
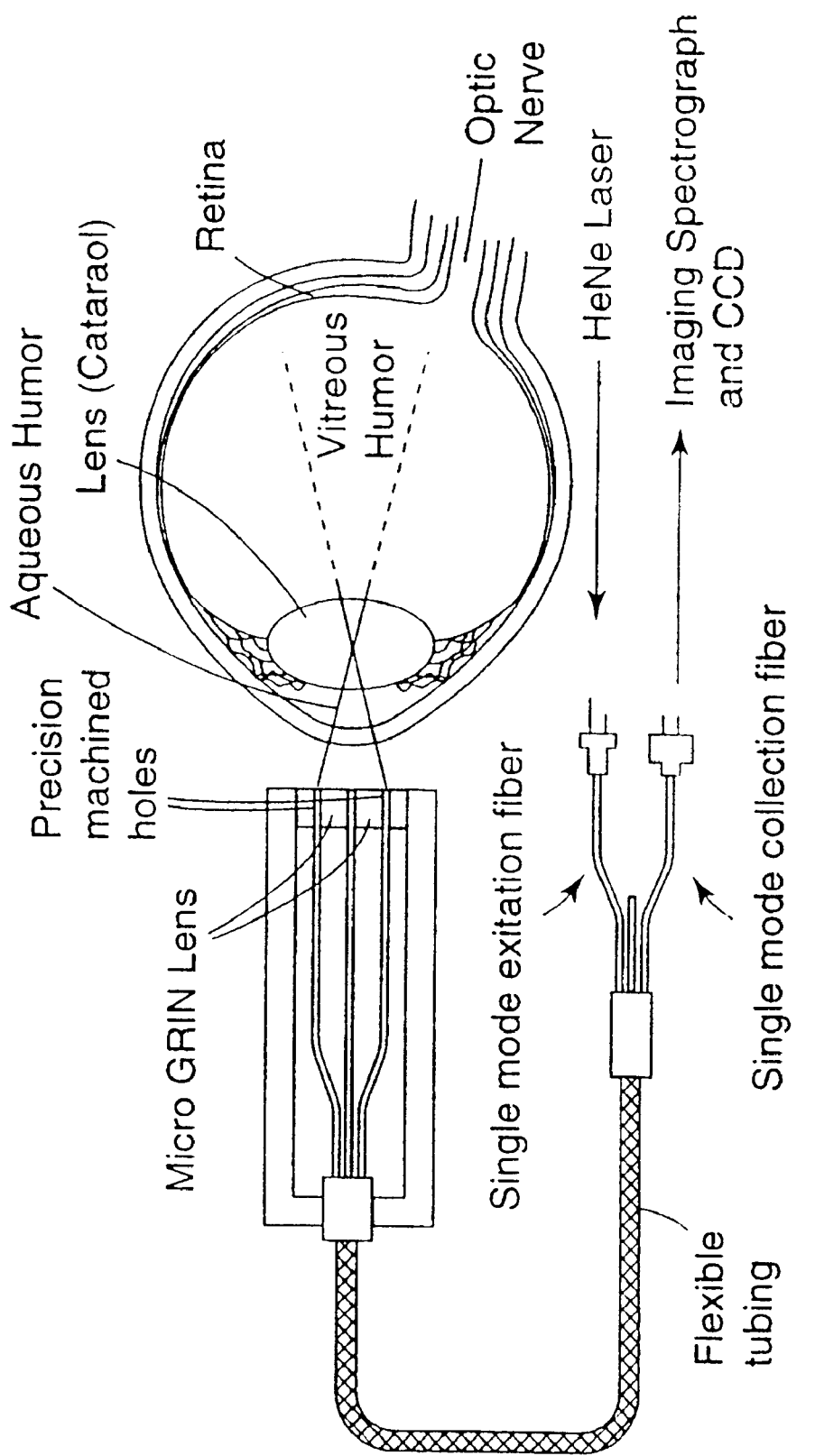
FIG. 1 is an illustration of the apparatus for the acquisition of in vivo Raman spectra.

The invention provides methods for the use of Raman spectroscopy to non-invasively detect molecular characteristics of the constituents of the aqueous humor, vitreous humor, lens or retina. The method can be employed for the detection of molecular changes underlying ocular pathologies. The non-invasive method provided by the invention makes use of techniques and equipment that enable detection of Raman spectra with light intensities that fall within acceptable safety standards.

Embodiments of the invention include methods of using Raman spectroscopy for detecting changes in the eye and identifying those changes associated with ocular pathologies such as diabetes. In preferred embodiments of the invention, the ocular pathology is a pre-cataract marker or a pre-retinopathy marker. In a specific embodiment of the invention, the method involves the steps of introducing light into the eye of the subject using a laser; collecting Raman spectra emitted from the eye; dispersing the collected Raman spectra onto a detector; and analyzing detected Raman spectra to quantify a molecular change related to an ocular pathology. In an illustrative embodiment of the invention, this method involves correlating the Raman spectra with traditional markers associated with known ocular pathologies. In a specific embodiment of the invention, the markers associated with ocular pathologies are blood glucose and insulin levels. In a variation of this embodiment, Raman spectroscopic measures obtained from a patient can be compared to a data set range of measures established from subjects with normal to severely pathological ocular measures in order to determine the status of the subject's condition. Such illustrative embodiments can be used to identify early disease states, to provide information on the long term status of the subject and to facilitate the early treatment of various pathologies.

Embodiments of the invention include methods for the non-invasive identification of molecular changes associated with ocular pathologies. One embodiment of this method consists of using a laser to introduce light into an eye of a subject having an ocular pathology, collecting Raman spectra emitted from the eye, dispersing the collected Raman spectra onto a detector, analyzing detected Raman spectra obtained from the subject and comparing the subject's spectral pattern to a normal spectral pattern, wherein differences between the subject's spectral pattern and the normal spectral pattern indicate an ocular pathology. In a specific embodiment of this method, the subject is a sand rat and the ocular pathology is diabetes induced ocular damage.

Embodiments of the invention can use a variety of lasers to introduce light into the eye of a subject. In preferred embodiments of the invention, the laser that is utilized is selected from the group consisting of HeNe, diode, Ti:Sapphire, Cr:Forsterite and Nd:YAG lasers. Lasers emitting light of various wavelengths are well known in the art. In one embodiment of the invention, the laser emits light of a visible red wavelength. In an alternative embodiment, the laser emits light of an infrared wavelength. In preferred embodiments, the laser emits light of a wavelength selected from the group consisting of about 600–700 nm; about 700–1300 nm; about 1200–1300 nm; and about 1550–1850 nm. In addition, different embodiments of the invention can focus light into various regions of the eye of a subject. In preferred embodiments, the light introduced into the eye is focused into the region of the eye selected from the group consisting of the lens, the vitreous humor, the aqueous humor and the retina.

Embodiments of the invention can evaluate a variety of molecular changes that may be associated with ocular pathologies. In preferred embodiments, the molecular changes are assessed by comparing the ratios of various moieties including the —OH stretching/—CH stretching ratio or the —SH/S—S ratio of lens proteins. In another embodiment, the molecular changes involve the C=C stretching or C—H stretching vibrations of vitreous proteins. In yet another embodiment, the molecular change comprises alterations in the concentrations of aqueous metabolites. In a related embodiment, the molecular change is the increase of products from non-enzymatic glycation of retinal proteins.

A variety of embodiments of the invention exist for the collection, dispersion and analysis of Raman spectra. In one embodiment, light is introduced and collected in an imaging mode. In an alternative embodiment, the light is introduced and collected in a non-imaging mode. In a specific embodiment, the light is introduced and collected through a graded index lens. In preferred embodiments of the invention, the Raman spectra collected are selected from the group consisting of the region in about 4000–200 $cm^{-1}$ and about 3000–500 $cm^{-1}$. In one embodiment of the invention, the collected light is dispersed onto a detector using a ruled grating. In another embodiment of the invention, the collected light is dispersed onto a detector using a holographic grating. In a specific embodiment of the invention, the detector is a red/blue enhanced CCD camera.

A variety of means for analyzing Raman spectral data are known in the art. In one embodiment involving the spectral data analysis step of the invention, the detected spectral data are analyzed using partial least squares. In an alternative embodiment, the detected spectral data are analyzed using principle component analysis.

As illustrated below, in addition to the above-mentioned illustrative embodiments, a wide variety of means for accomplishing the different steps of the invention are contemplated.

A. Detection of Molecular Changes of the Eye Using Raman Spectroscopy

1. Introduction of Light Into the Eye of the Subject Using a Laser

The invention provides a method for non-invasive detection of ocular pathology in a subject. The method comprises the introduction of light into the eye of the subject using a laser. The useful spectral range extends from the long wavelength visible (red) into the near infrared. The wavelength of light which is introduced into the eye can be selected to minimize scattering and fluorescence, as well as minimizing water absorption to maximize the signal which will ultimately be collected. Water absorption limits the technique beyond 1850 nm and also in a band around 1400 nm. Thus, the useful spectra wavelength ranges are from about 600–700 nm in the visible red range, and 700–1300 nm and 1550–1850 nm in the infrared range. In one embodiment, the light is infrared. The preferred wavelength is about 1200–1300 nm. Different sources for a particular wavelength of light may be selected. Examples of lasers that can be used as a light source in the method include, but are not limited to, helium: neon (HeNe), diode, titanium: sapphire (Ti:Sapphire), chromium: forsterite (Cr:Forsterite), and neodymium: yttrium aluminum garnet (Nd:YAG). In some embodiments of this invention the laser used to introduce light into the eye comprise an infrared wavelength producing laser, including, but not limited to a 632.8 nm HeNe laser, 700–900 nm Ti:Sapphire laser, 1150–1300 nm Cr:Forsterite laser and 1064 nm, 1300 nm, 1500 nm or 1600 nm Nd:YAG laser.

The lens through which light is introduced into the eye can be selected to minimize the illumination and collection volumes, thereby avoiding light intensities too high for compliance with safety standards. In one embodiment, the light is introduced into the eye by a non-spatially selective fiber bundle. This configuration provides a non-imaging mode of detection and can detect relatively weak signals from the target, at the expense of spatial resolution of the signal. In one preferred embodiment, the light introduced into the eye is coupled into a single mode optical fiber using a microscope objective. This configuration provides an imaging mode of detection and can maximize the spatial resolution of the signal from a particular target in the eye, at the expense of sensitivity to the signal. The light can be passed through a line pass filter to prevent HeNe plasma lines from reaching the sample. Graded index (GRIN) lenses can be incorporated at the distal tip of the optical fiber bundle to obtain spatially resolved Raman spectra at reduced light levels. The use of GRIN lenses has been described by Ansari and Suh R. (R. Ansari et al., 1996, Ophthalmic Technologies VI, pp. 12–20; R. R. Ansari et al., 1996, Lasers in Ophthalmology III, pp. 62–72; R. R. Ansari and K. I. Suh, 1996, Optical Diagnostics of Living Cells and Biofluids, Vol. 2678).

When light is introduced into the eye in accordance with the invention, it can be targeted to a region of the eye for examination of the molecular status of proteins within the targeted region. Targets can include, but are not limited to, the aqueous humor, vitreous humor, lens or retina. Raman spectral measurements from any one of these targets will reflect the molecular status of proteins in the target region examined.

2. Collection of Raman Spectra Emitted From the Eye

The method for non-invasive detection of ocular pathology in a subject further comprises collecting Raman spectra emitted from the eye. Various means for collecting and analyzing Raman spectra are well known in the art including those disclosed in U.S. Pat. Nos. 5,751,415 and 5,048,959, which are incorporated herein by reference. In some embodiments of the invention, a spectrograph that will spectrally disperse input light and provide at the output plane the resulting spectra is sufficient. Alternatively, an imaging spectrograph which adds the feature that the tall axis of the slits is imaged onto the spectral plane may be utilized. With imaging spectrographs, there is a one to one relationship of slit and the 'height' of the image. Thus individual fibers introducing light at the input slit of an imaging spectrograph will appear as stripes of spectrally dispersed light at the exit plane, with the width of the stripe representing the diameter of the fiber.

In one embodiment of the invention, the light which was emitted from an imaging or non-imaging mode of introduction is collected through a graded index lens (GRIN). The Raman spectra collected are preferably in the region of about 4000 to about 200 $cm^{-1}$ and more preferably in the region of about 3000 to about 500 $cm^{-1}$.

3. Dispersion of the Raman Spectra Onto a Detector

The method for non-invasive detection of ocular pathology in a subject further comprises dispersing the collected Raman spectra onto a detector. In one embodiment the collected light is dispersed onto a detector using a conventional ruled grating. In the preferred embodiment, the light is collected and dispersed onto a detector using a holographic grating. Examples of detectors are, but are not limited to, photomultipliers, reticon arrays, diode arrays or charge coupled device (CCD) cameras. In one embodiment, the detector is a red/blue enhanced CCD camera. Thermoelectric cooling of the camera improves signal-to-noise ratio. For example the camera may be cooled to, but is not limited to being cooled to $-40°$ C.

4. Analysis of Detected Raman Spectra to Quantify Molecular Changes

Raman spectroscopy is a sensitive technique for monitoring biochemical changes, allowing for the detection of molecular changes in such ocular structures as aqueous, vitreous and the lens. Raman spectra exhibit distinctive features that are molecule specific. Raman scattering is inelastic-the molecular bonds of the species under study scatter the incoming optical radiation and slightly change its wavelength. The differential energy is converted into vibrational energy of the molecule. In most cases, the spectrographic signal (monitoring the scattered radiation at a specific shift with respect to the incident radiation) is measured by recording the accumulated detector reading (in arbitrary units) at that (shifted) wavelength. Often the background/stray light is subtracted. A meaningful indicator is frequently the ratio between the two spectral peaks. In most cases there is no quantified threshold for these ratio or other spectroscopic values. That is, changes in molecular bonds of the species under study are taken as relative to baseline.

Analysis of the data collected based on the spectrographic signal can reveal whether a protein environment is normal or pathogenic. For example, lens hydration is thought to be directly related to the formation of lens opacities which result in cataract formation. Therefore, Raman spectral analysis of the hydration levels of lens proteins can provide a method to detect pre-cataract markers. This early detection permits a patient to receive treatment to slow or prevent the progression of the pathology prior to the onset of irreversible physical changes. Similarly, increased concentrations of advanced glycation products are thought to be related to increased nonenzymatic glycation in retinopathy patients. Therefore, Raman spectral analysis of the levels of advanced glycation products can provide a method to detect pre-retinopathy markers.

Raman spectroscopy can be used to identify a wide range of different molecular changes which can be correlated to ocular pathology. Specifically, Raman spectroscopy can be used to identify early markers of diabetes or diabetes-induced ocular pathology, or markers of advanced progression of a diabetes induced ocular pathology. Generally, a catalog of Raman spectra collected from subjects with normal ocular history and subjects with known pathological ocular history can be compiled for comparison against subjects with unknown ocular conditions. Raman peaks in each sample will be compared with the catalog database in order to determine if peaks in the unknown sample are more similar to the normal or pathological condition. Studies have shown that changes in Raman peaks at various points (on the spectrum) change with pathology of the ocular target studies. Examples of changes in the Raman spectra which occur with ocular pathology, but to which this invention is not limited, are discussed below.

A variety of biochemical conditions may be evaluated using the Raman spectroscopy techniques described herein. Raman spectroscopy can be used to detect alterations in lens hydration as a result of hyperglycemic stress, a phenomenon that is thought to be directly related to the formation of lens opacities. In particular, the Raman peak in lens spectra corresponding to the O—H stretching mode (denoting water) can be compared to that of the C—H stretch (denoting protein) to monitor hydration of lens proteins (A. Mizuno and Y. Ozaki, 1991, Lens and Eye Toxicity Research 8:177–187). An increase in the ratio of —OH/—CH or a reduction in the —SH/—S—S ratio is indicative of an increase in lens hydration. Specifically, increases in lens hydration are indicative of early lens opacification (A. Mizuno and Y. Ozaki, 1991, Lens and Eye Toxicity Research 8:177–187).

Similarly, advanced glycation products that correspond to increased nonenzymatic glycation in retinopathy patients can be resolved in Raman spectra of vitreous samples. When light is focused into the vitreous humor, the collected Raman spectra will reflect the C=C stretching or C—H stretching vibrations of vitreous proteins. In the embodiments of this invention where light is focused into the retina the Raman spectra can detect changes in advanced glycation products. An increase in advanced glycation products will generate a larger spectrographic signal and be indicative of increased nonenzymatic glycation and of retinopathy. For example, studies of vitreous of patients with diabetic retinopathy have demonstrated increased Raman peaks at 1604 and 3057 $cm^{-1}$ corresponding to the stretch vibrations of C=C and C—H molecules (J. Sebag, et al., 1994, Invest. Opthalmol. Vis. Sci., 35, 2976–2980).

When light is focused into the aqueous humor, the Raman spectra can detect various aqueous metabolites (see e.g. J. Wicksted, et al., 1995, Appl. Spec., 49, 987–93). For example, Raman scattering can be used to observe the metabolic concentrations of molecules including glucose, lactate and urea. Two positions of a grating as discussed above can be used for the different laser excitation wavelengths. In particular, lower frequency ranges can be used to study the C—N stretching vibration of urea as well as the C—COOH peak of lactic acid, while higher ranges can be used to observe the $CH_2$ and $CH_3$ stretches of glucose and lactate, respectively.

The method for non-invasive detection of ocular pathology in a subject further comprises analyzing the detected Raman spectra to quantify a molecular change related to ocular pathology. A variety of techniques for analyzing Raman spectral data are known in the art. For example, a multivariate statistical method can be used to obtain predictive information based on the detected spectra. In one embodiment, the detected spectral data are analyzed using partial least squares (PLS; A. J. Durkin, et al., 1998 Lasers in Medical Science). In another embodiment, principle component analysis (PCA; S. Wold, et al., 1987 Chemometrics and Intelligent Laboratory Systems 2:37–52) may be utilized to analyze the data.

In analyses employing the method of partial least squares (PLS) to analyze detected spectra, PLS may be employed to develop an empirical linear model of Raman scattering in samples using a training set with known concentrations of various analytes and optical properties similar to those considered as unknowns (A. J. Durkin, et al. (1993), Applied Spectroscopy 47:2114–2121). For example, efforts have been made to quantify chromophores in biological samples using PLS, where work has focused on the determination of blood glucose levels using FT-IR techniques. These studies show the determination of quantitative information from optical spectra both in vitro and in vivo. (M. R. Robinson, et al. (1992), Clinical Chemistry 38:1618–1622; D. M. Haaland (1990) New York: Academic Press 395–368).

The PLS method is based on the regression between two matrices, X and Y, using the notation of Malinowski (E. R. Malinowski (1991), New York John Wiley and Sons, Inc. 169–172). Specifically, for spectroscopic analysis of n mixtures (sample) with p unknowns (constituents of interest), X and Y represent spectral and concentration matrices respectively. Through a sequence of matrix rotations and regression steps, which for the simplest case can be described as a singular value decomposition, PLS seeks to relate the matrix of spectra, X, to the matrix of concentrations of the constituent of interest, Y, via a calibration or model matrix B such that $$\underset{n \times p}{Y} = \underset{n \times m}{X} \underset{m \times p}{B}$$

where B is set of calibration constants for the system. The rows of X and Y contain information about n sample mixtures. The columns of X contain emission spectra at m spectral wavelengths. Although samples may contain many constituents, the rows of Y are composed only of the concentrations of the p known constituents of interest for each sample. The reader is referred to a description of Nonlinear Iterative Partial Least Squares (NIPALS) discussed in E. R. Malinowski (1991) supra, for an accurate and detailed description of PLS mechanics in its least complex manifestation.

The accuracy of prediction for PLS is effected by the composition of the training and validation sets as well as the spectral information included in the data (A. J. Durkin et al. (1994), Proceedings from The Conference on Lasers and Electro-optics (CLEO) May). One technique used to assess the accuracy of prediction and to select the optimum number of factors to retain in the model is known as the method of cross-validation (D. M. Haaland (1990) supra; E. R. Malinowski (1991) supra). This technique evaluates the ability of a PLS calibration model to predict the concentrations of unknown spectra as a function of the rank (number of factors or principal components) used in creating the calibration model.

An attractive facet of PLS is that it does not explicitly require a priori knowledge of the sample optical properties but instead can use spectra from a training set of samples with known concentrations and with chemical complexity similar to the unknown sample of interest (D. M. Haaland (1990) supra; A. J. Durkin et al. (1994) supra; E. V. Thomas et al. (1990), Analytical Chemistry 62:1091–1099). Consequently, the application of PLS methods to Raman spectra, presents a useful tools as a method for optical determination of tissue biochemistry.

In one embodiment using PLS studies, calibration and data acquisition can be performed using Kestrel Spec software (Rhea Corp.). In this embodiment of the invention, a 632.8 mn neon line can be used with the single point calibration routine provided in this software. Reproducibility of the calibration can be verified using the plasma lines which are permitted to reach the detector upon removal of the line pass filter. The integration time for each acquired spectrum can be 1 second with a total of 200 accumulated spectra per sample. In order to simulate a device that would not compromise the integrity of whole blood cells, data collection parameters can be loosely based on parameters used by various other groups involved in Raman studies of tissues (C. J. Franck, et al. (1993), Applied Spectroscopy 47(4):387–390; A. Mahadevan-Jansen, et al. (1996), Journal of Biomedical Optics 1(1):31–70). In such techniques, one can account for slowly varying fluctuations in laser power over the course of the experiment. To do this, a "standard" Raman spectra can be acquired, using parameters identical to those used for the turbid samples, from a cuvette containing pure 200 centistokes PDMS every 15 minutes. This can be used to normalize the turbid spectra taken in each 15 minute segment. Data can then be exported to Microsoft Excel and combined to form matrices. MATLAB (the Math Works, Natick Mass.) can subsequently be used to execute PLS and cross-validation routines.

Figure 2:
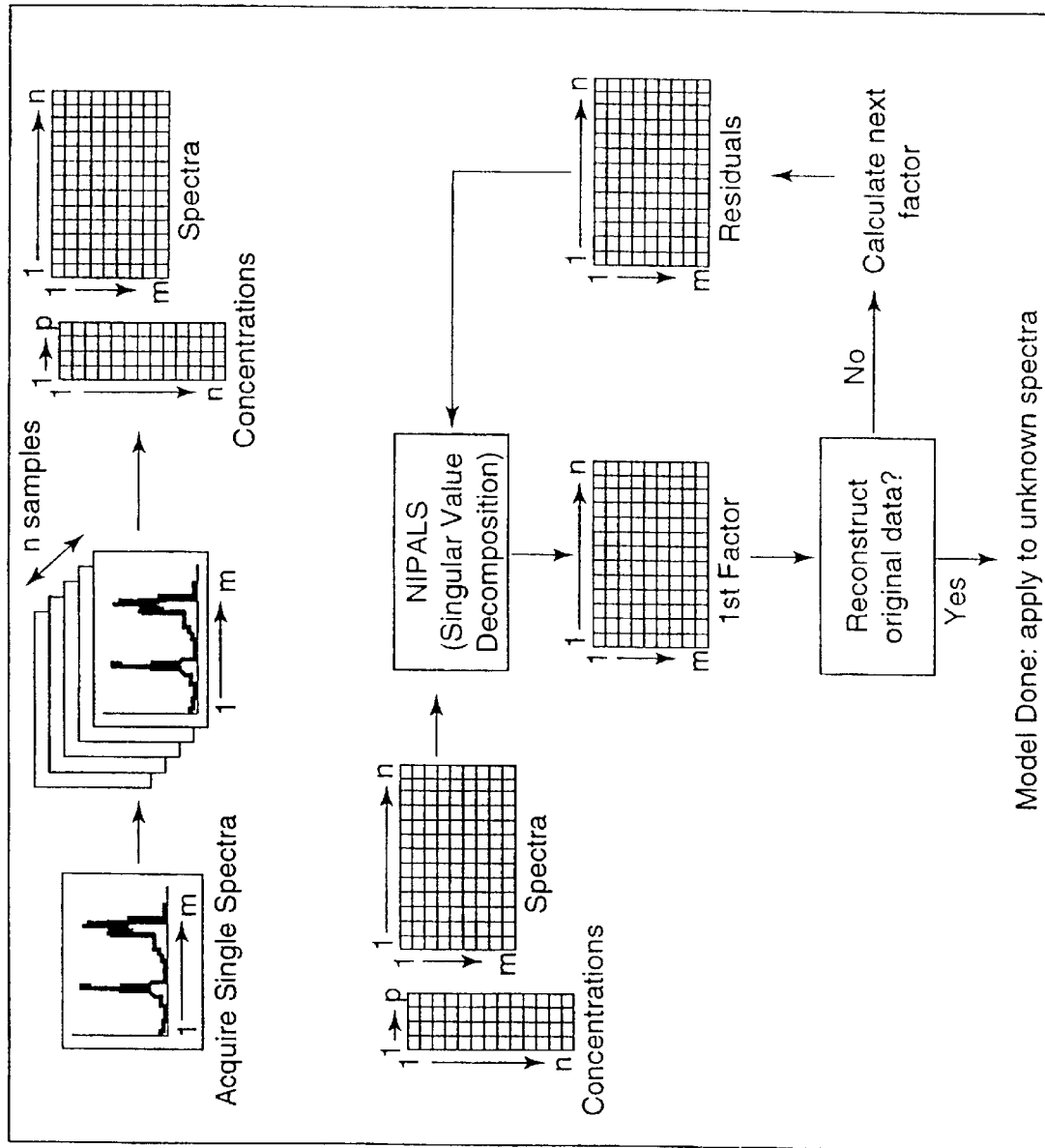
FIG. 2 is a block diagram of the flow of the nonlinear iterative Partial Least Squares algorithm.

Data from the samples can be analyzed using a PLS algorithm from the MATLAB Chemometrics Toolbox. A block diagram depicting the important steps in the analysis method used here is shown in FIG. 2. The most accurate prediction model for the training data can be chosen using a cross-validation algorithm which can iteratively construct a model for N−1 spectra was then decomposed into principal components, or factors, using singular value decomposition (D. M. Haaland, et al. (1988), Analytical Chemistry 60:1193–1202). Models can be built using a successively increasing number of these factors. On the first iteration, the model can consists of only the factor that accounts for most of the variance in the data (indicated by the magnitude of the corresponding eigen value). The model for each factor level can be applied to the "unknown" spectrum to predict the concentration of the component of interest and the prediction error can be recorded in a matrix for future reference. The next most important factor (indicated by the magnitude of the corresponding eigen value) can subsequently be included in the model and the prediction process repeated until a model consisting of all factors resulting from the decomposition of the N−1 training set can be employed. The "unknown" can then be returned to the training data and a different spectrum can be selected as the "unknown". This entire process can be repeated until all samples play the role of "unknown" once. The prediction error for each factor level can then be summed across the sample set and plotted. The model for the entire set can then be constructed using the factor level for which the residuals across the sample set are minimized. Models consisting of the "optimum" number of factors+1 and the "optimum" number of factors−1 can also be constructed. These models can also be applied to the data and the predictions compared to the results obtained using the "optimum" number of factors.

As an alternative to the PLS, the detected spectra can be analyzed using other techniques such as neural networks (see e.g. Durkin and M. N. Ediger, 1998 SPIE-Least Invasive Diagnostics, 3253–3254). Specifically, variables such as the substance concentration of a biological analyte or analytes can be determined by comparing the Raman spectral characteristics of the sample with a comparative model, in particular, an artificial neural network discriminator (ANND) that can be trained with a plurality of Raman spectral characteristics from biological fluids or tissue possessing known Raman scattered light intensities versus wavelength characteristics at known concentrations. A preferred implementation of the ANND employs fuzzy adaptive resonance theory-mapping (ARTMAP), which has noise rejection capabilities and can readily handle nonlinear phenomena. An illustrative example of the determinations of concentrations of biological substances using Raman spectroscopy and artificial neural network discriminators is described in U.S. Pat. No. 5,553,616 which is incorporated herein by reference.

B. Correlation of Ocular Raman Spectroscopic Measures With Blood Glucose and Insulin Levels A subject's eyes can be evaluated using Raman spectroscopic measurements of lens, aqueous humor or vitreous humor as described above and can also be evaluated for traditional measures of diabetes and diabetes-induced ocular pathology. Collected spectral data can be subjected to a multivariate statistical analysis. A data set and algorithm can be developed for using Raman spectroscopy to diagnose diabetes or diabetes-induced ocular pathology in humans using an approach based on that established in the animal model described in Example 2 below.

Traditional indicators of diabetes include abnormal levels of blood glucose and insulin and ocular damage. Blood can be drawn from the subject to determine levels of glucose and insulin. Glucose can be measured, for example, using a glucose oxidase immunoassay of a whole blood sample. Insulin can be measured using, for example, enzyme immunoassay methods of a blood serum sample.

An ophthalmic exam can be administered to determine if the subject has any ocular damage. The pupils of the subject can be dilated to facilitate the exam. The ophthalmic exam can include examining the eye for the presence of cataracts. If the subject has a cataract, it can be graded as: grade 0 (lens completely clear), grade 1 (opaque areas at lens periphery, vascular features of the retina still visible), grade 2 (widespread distribution of opaque areas within the lens, vascular features of the retina obscured), grade 3 (lens totally opaque, cataract visible as dense white mass to the naked eye). The vasculature of the retina and intraocular pressure can also be examined. Finally, the visual acuity of the subject can be tested using a standard vision chart.

Data from each subject can be compiled such that a profile of measures of Raman spectral features can be correlated with measures obtained by any or all of the above-described or other methods of blood chemistry and ophthalmic examination. Analysis of these data permit the identification of alterations in the Raman spectra of a diabetic or pre-diabetic subject which precede physical changes previously identified by ophthalmic exam only after the development of irreversible ocular damage.

C. Method of Predicting Diabetes in a Human Subject Using Raman Spectroscopy of the Eye As described above, one can develop a data set and an algorithm for analysis of data for human subjects, and then use single subject Raman spectrographic measures to diagnose or predict the onset or stage of progression of diabetes-induced ocular pathology. The Raman spectroscopic data obtained for a patient can be compared to a data set range of measures established from subjects with normal to severely pathological ocular measures and the algorithm applied to determine the status of the subject's condition. Where a subject's Raman spectrographic measures are found to be indicative of the early onset of an ocular pathology, that subject can then be treated to prevent permanent ocular damage.

EXAMPLES

The following examples are presented to illustrate the present invention and to assist one of ordinary skill in making and using the same. The examples are not intended in any way to otherwise limit the scope of the invention.

Example 1

Detection of Diabetes-Induced Molecular Changes of the Eye Using Raman Spectroscopy.

One method for the detection of diabetes-related ocular pathologies involves the use of Raman spectroscopy to non-invasively monitor changes in the molecular constituents of the lens, vitreous humor, aqueous humor or retina. Ideally this method is employed to screen for early markers of ocular molecular pathologies so that permanent damage to the eye can be circumvented by preventative drug therapy. This example demonstrates a method by which Raman spectroscopy can be used to detect such changes.

An optical probe is used to introduce light into and collect light emitted from a subject's eye (FIG. 1). Light is focused into the lens, vitreous humor, aqueous humor or retina of the subject. The source of light introduced into the eye is a 632.8 nm helium neon (HeNe) laser (Spectra-Physics 127). This light is coupled into a single mode optical fiber using a microscope objective and is passed through a line pass filter to prevent HeNe plasma lines from reaching the sample. Graded index (GRIN) lenses are incorporated at the distal tip of the optical fiber bundle to obtain spatially resolved Raman spectra at reduced light levels.

As light is collected from the eye via the optical fiber, it is passed through a line filter (Kaiser Super Notch, 6 OD, 632.8 nm) to prevent Rayleigh scattered light from reaching the detector. Collected light (Raman spectra) enters the spectrograph (SPEX 270 f/4, slit size=50 mm) and is dispersed across the face of a CCD detector using a holographic grating (blaze angle=630 nm, 1200 groves/mm, RLD: 3.1 nm/mm). The detector is an intensified red/blue enhanced CCD camera (Princeton Instruments ICCD-567G/RBT, 576×384 array, pixel size=22×22 mm, active area=12.7×8.4 mm, peak quantum efficiency=40%) which is thermoelectrically cooled to an operating temperature of −40° C. to improve signal/background ratio.

Calibration and data acquisition is performed using Kestrel Spec software (Rhea Corp.) single point calibration routine for 632.8 nm neon light. The integration time for each acquired spectrum is optimized to obtain the best signal to noise ratio while minimizing the exposure of the eye to laser light. Data is subsequently exported to Microsoft Excel and combined to form matrices. MATLAB (the Math Works, Natick Mass.) is used to perform multivariate statistical analysis of the data.

The Raman spectra collected exhibit distinctive features that are molecule specific, depending upon the region of the eye into which the light is focused. Where the light is focused into the lens of the subject, the Raman peak in lens spectra corresponding to the O—H stretching mode (water)/C—H stretch (protein) ratio may be analyzed to determine the hydration state of lens proteins. Where the light is focused into the vitreous humor of the subject, the level of advanced glycation products may be analyzed as an indication of the level of nonenzymatic glycation.

Example 2

Development and Optimization of an Algorithm for the Prediction of Diabetes-Induced Ocular Molecular Changes in an Animal Model.

One method for the early diagnosis or indication of the progression of diabetes in a subject is the detection of ocular molecular changes by Raman spectroscopy. The correlation of molecular changes of the eye associated with the progression from normal to diabetic conditions can be evaluated. This example demonstrates a method by which an algorithm can be created based on this correlation such that ocular Raman spectra measurements alone may be used to predict if a subject has diabetes and, if so, the level of progression of the disease.

The subjects used in an animal model are female sand rats (*Psammomys obesus*). This animal model is chosen because this strain of rat develops nutritionally-induced diabetes. Manipulation of the sand rat's diet has been shown to result in a slow onset and progression of diabetes. This model is more similar to the progression of diabetes observed in humans than other animal models which use pharmaceuticals to induce an abrupt diabetic condition.

Rats are divided into a control group (fed non-diabetogenic, low carbohydrate/high fiber sand rat chow diet (BioScrv/Voight diet)) and the experimental group (fed diabetogenic diet (Purina 5002 rodent chow diet)). Rats are sacrificed each month for 12 months in order to examine the progression of diabetes-induced changes in these animals.

In order to examine the diabetes-induced changes over time, animals are coordinately evaluated for traditional measures of diabetes and diabetes-induced ocular pathology. Traditional indicators of diabetes include abnormal levels of blood glucose and insulin and ocular damage.

Blood is drawn from each animal every two weeks to determine levels of glucose and insulin. Glucose is measured using a glucose oxidase immunoassay of a whole blood sample. Insulin is measured using enzyme immunoassay of a blood serum sample.

An ophthalmic exam for cataract formation is administered every two weeks. The pupils are dilated with application of Mydriacyl 5g/l (Tropicamide, ophthalmic solution, USP, 0.5%) to facilitate the exam. If the subject has a cataract, it is graded as: grade 0 (lens completely clear), grade 1 (opaque areas at lens periphery, vascular features of the retina still visible), grade 2 (widespread distribution of opaque areas within the lens, vascular features of the retina obscured), grade 3 (lens totally opaque, cataract visible as dense white mass to the naked eye). Histological samples of the eyes and pancreas are collected from each animal at necropsy and evaluated for pathological histology.

Additionally, Raman spectroscopy of the eye is performed prior to sacrificing of each animal as described in Example 1. Aqueous and vitreous humor samples are collected prior to euthanasia for additional in vitro spectroscopic analysis.

Data from each subject are compiled such that a data set profile of ocular measures of Raman spectral features may be correlated with measures obtained by blood chemistry and ophthalmic examination made at different timepoints in the progression of diabetes in this animal model. Multivariate statistical methods (e.g., Principal Component Analysis (PCA), the method of Partial Least Squares (PLS), etc.) are used to establish an algorithm from which Raman spectrographic measures from a subject can be used to accurately diagnose the onset and progression of a subject's diabetes or diabetes-induced ocular pathology.

The algorithm is selected such that it has the maximum sensitivity to pathological Raman spectrographic measures in comparison to normal measures, while minimizing the false positive identification of normal Raman spectra measures as pathological. Further, the algorithm is selected to distinguish between different stages in the progression of diabetes-induced ocular pathology. In order to accomplish this, several parameters are considered in analyzing the data, including but not limited to: (1) intrasubject variability; (2) calibration of the instrumentation with standards for each Raman measure to be examined; (3) transformation of raw data to reflect the weight of each variable measured in the diagnostic prediction of pathology; and (4) probability that a given measure exists within a particular diagnostic category (Ramanujam et al., 1996, Lasers in Surgery and Medicine 19:46–62).

What is claimed is:

1. A method for non-invasive detection of an ocular pathology in a subject comprising:
   (a) introducing light into the eye of the subject using a laser;
   (b) collecting Raman spectra emitted from the eye;
   (c) dispersing the collected Raman spectra onto a detector;
   (d) analyzing detected Raman spectral data to identify a molecular change associated with the ocular pathology,
   wherein the ocular pathology comprises a pre-cataract marker or a pre-retinopathy marker.

2. The method of claim 1, wherein the laser is a HeNe, diode, Ti:Sapphire, Cr:Forsterite or Nd:YAG.

3. The method of claim 2, wherein the molecular change is:—OH stretching/—CH stretching ratio or—SH/S—S ratio of lens proteins.

4. The method of claim 1, wherein the laser emits light of a visible red wavelength.

5. The method of claim 4, wherein the molecular change is C=C stretching or C—H stretching vibrations of vitreous proteins.

6. The method of claim 1, wherein the laser emits light of an infrared wavelength.

7. The method of claim 6, wherein the molecular change comprises alterations in concentrations of metabolic molecules.

8. The method of claim 1, wherein the laser emits light of a wavelength of about 600–700 nm.

9. The method of claim 8, wherein the molecular change is the increase of products from non-enzymatic glycation of retinal proteins.

10. The method of claim 1, wherein the laser emits light of a wavelength of about 1200–1300 nm.

11. The method of claim 1, wherein the light introduced into the eye is focused into the lens.

12. The method of claim 1, wherein the light introduced into the eye is focused into the vitreous humor.

13. The method of claim 1, wherein the light introduced into the eye is focused into the aqueous humor.

14. The method of claim 1, wherein the light introduced into the eye is focused into the retina.

15. The method of claim 1, wherein the ocular pathology is a pre-cataract marker.

16. The method of claim 1, wherein the ocular pathology is a pre-retinopathy marker.

17. The method of claim 1, wherein the Raman spectra collected are in about the 4000–200 cm$^{-1}$ region.

18. The method of claim 1, wherein the Raman spectra collected are in the region about 3000–500 cm$^{-1}$.

19. The method of claim 1, further comprising the step of correlating the Raman spectra with non-Raman based markers associated with ocular pathologies.

20. The method of claim 1, wherein the light is introduced and collected in an imaging mode.

21. The method of claim 1, wherein the light is introduced and collected in a non-imaging mode.

22. The method of claim 1, wherein the light is introduced and collected through a graded index lens.

23. The method of claim 1, wherein the collected light is dispersed onto a detector using a ruled grating.

24. The method of claim 1, wherein the collected light is dispersed onto a detector using a holographic grating.

25. The method of claim 1, wherein the detector is a red/blue enhanced CCD camera.

26. The method of claim 1, wherein the spectral data are analyzed using partial least squares.

27. The method of claim 1, wherein the spectral data are analyzed using principle component analysis.

28. The method of claim 1, wherein the laser emits light of a wavelength of about 700–1300 nm or 1550–1850 nm.

29. A method for non-invasive detection of an ocular pathology in a subject comprising:

(a) introducing light into the eye of the subject using a laser;

(b) collecting Raman spectra emitted from the eye;

(c) dispersing the collected Raman spectra onto a detector;

(d) analyzing detected Raman spectral data to identify a molecular change associated with the ocular pathology; the molecular change comprising:
—OH stretching/—CH stretching ratio;
—SH/—S—S ratio of lens proteins;
C=C stretching vibrations of vitreous proteins; or
C—H stretching vibrations of vitreous proteins.

30. The method of claim 29, wherein the molecular change is —OH stretching/—CH stretching ratio.

31. The method of claim 29, wherein the molecular change is —SH/—S—S ratio of lens proteins.

32. The method of claim 29, wherein the molecular change is C=C stretching vibrations of vitreous proteins.

33. The method of claim 29, wherein the molecular change is C—H stretching vibrations of vitreous proteins.

34. The method of claim 29, wherein the laser emits light of a visible red wavelength.

35. The method of claim 29, wherein the laser emits light of an infrared wavelength.

36. The method of claim 29, wherein the laser emits light of a wavelength of about 600–700 nm.

37. The method of claim 29, wherein the laser emits light of a wavelength of about 700–1300 nm or 1550–1850 nm.

38. The method of claim 29, wherein the laser emits light of a wavelength of about 1200–1300 nm.

39. The method of claim 29, wherein the light introduced into the eye is focused into the lens.

40. The method of claim 29, wherein the light introduced into the eye is focused into the vitreous humor.

41. The method of claim 29, wherein the light introduced into the eye is focused into the aqueous humor.

42. The method of claim 29, wherein the light introduced into the eye is focused into the retina.

43. The method of claim 29, wherein the Raman spectra collected are in about the 4000–200 cm$^{-1}$ region.

44. The method of claim 29, wherein the Raman spectra collected are in the region about 3000–500 cm$^{-1}$.

45. The method of claim 29, further comprising the step of correlating the Raman spectra with non-Raman based markers associated with ocular pathologies.

46. The method of claim 29, wherein the light is introduced and collected in an imaging mode.

47. The method of claim 29, wherein the light is introduced and collected in a non-imaging mode.

48. The method of claim 29, wherein the light is introduced and collected through a graded index lens.

49. The method of claim 29, wherein the collected light is dispersed onto a detector using a ruled grating.

50. The method of claim 29, wherein the collected light is dispersed onto a detector using a holographic grating.

51. The method of claim 29, wherein the detector is a red/blue enhanced CCD camera.

52. The method of claim 29, wherein the spectral data are analyzed using partial least squares.

53. The method of claim 29, wherein the spectral data are analyzed using principle component analysis.

\* \* \* \* \*